United States Patent
Dennis et al.

(10) Patent No.: US 8,759,392 B2
(45) Date of Patent: Jun. 24, 2014

(54) AMIDES AS INHIBITORS OF HUMAN SECRETED PHOSPHOLIPASE A2

(75) Inventors: Edward A. Dennis, La Jolla, CA (US); George Kokotos, Athens (GR); Violetta Constantinou-Kokotou, Athens (GR); Samuel David, Dorval (CA)

(73) Assignee: The Regents of the University of California, Oakland, CA (US)

( * ) Notice: Subject to any disclaimer, the term of this patent is extended or adjusted under 35 U.S.C. 154(b) by 253 days.

(21) Appl. No.: 12/994,136

(22) PCT Filed: Jul. 21, 2009

(86) PCT No.: PCT/US2009/051307
§ 371 (c)(1),
(2), (4) Date: Jan. 20, 2011

(87) PCT Pub. No.: WO2010/011686
PCT Pub. Date: Jan. 28, 2010

(65) Prior Publication Data
US 2011/0111478 A1 May 12, 2011

Related U.S. Application Data

(60) Provisional application No. 61/083,494, filed on Jul. 24, 2008.

(51) Int. Cl.
*A61K 31/225* (2006.01)
(52) U.S. Cl.
USPC .............................. 514/547; 554/36
(58) Field of Classification Search
USPC .............................. 514/547; 554/36
See application file for complete search history.

(56) References Cited

FOREIGN PATENT DOCUMENTS

| WO | WO02/08189 | * | 1/2002 |
| WO | WO 02/08189 A1 | | 1/2002 |
| WO | WO 2005/107767 A2 | | 11/2005 |

OTHER PUBLICATIONS

Hansford et al., ChemBioChem, pp. 181-185, 2003.*
Antonopoulou et al., "Structure-Activity Relationships of Natural and Non-Natural Amino Acid-Based Amide and 2-Oxoamide Inhibitors of Human Phospholipase $A_2$ Enzymes," *Bioorg. Med. Chem.* (2008), 16:10257-10269, Elsevier Ltd.

(Continued)

*Primary Examiner* — Deborah D Carr
(74) *Attorney, Agent, or Firm* — DLA Piper LLP (US)

(57) ABSTRACT

Methods and compounds useful for inhibiting a phoshpolipase $A_2$ are provided, the methods comprising contacting the phoshpolipase $A_2$ with a compound having the structure A, or pharmaceutically acceptable salts thereof: wherein $R^1$ is H, F, $NH_2$, or COOH; $R^2$ is, H, linear saturated or unsaturated alkyl, alkenyl, or alkynyl; each of $R^3$ and $R^4$ is independently H, linear saturated or unsaturated alkyl, alkenyl, alkynyl, phenyl, or substituted phenyl; $R^5$ is H, $(C_1-C_6)$ alkyl such as methyl or ethyl; X is aryl or substituted aryl, such as phenyl or a substituted phenyl; and Y is O or S.

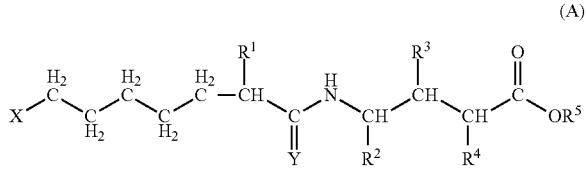

6 Claims, 5 Drawing Sheets

(56) References Cited

OTHER PUBLICATIONS

Gregory et al., "Inhibitors of Cyclo-Oxygenase-2 and Secretory Phospholipase A2 Preserve Bone Architecture Following Ovariectomy in Adult Rats," *Bone* (2006), 39:134-142, Elsevier.

Hansford et al., "D-Tyrosine as a Chiral Precursor to Potent Inhibitors of Human Nonpancreatic Secretory Phospholipase $A_2$ (IIa) with Antiinflammatory Activity," *Chem. BioChem.* (2003), 4:181-185, Wiley-VCH Verlag GmbH & Co. KGaA, Weinheim, Germany.

\* cited by examiner

AMIDES AS INHIBITORS OF HUMAN SECRETED PHOSPHOLIPASE A2

CROSS REFERENCE TO RELATED APPLICATIONS

This application is a 35 USC §371 National Stage application of International Application No. PCT/US2009/051307 filed Jul. 21, 2009, which claims the benefit under 35 USC §119(e) to U.S. application Ser. No. 61/083,494 filed Jul. 24, 2008, now expired. The disclosure of each of the prior applications is considered part of and is incorporated by reference in the disclosure of this application.

GRANT INFORMATION

This invention was made with government support under Grant No. GM20501 awarded by the National Institutes of Health. The government has certain rights in the invention

BACKGROUND OF THE DISCLOSURE

1. Field of the Disclosure

The present disclosure relates generally to compounds useful for the inhibition of human secreted phospholipase $A_2$. More specifically, the disclosure relates to the use of certain amides derived from non-natural amino acids as inhibitors.

2. Background Information

The phospholipase $A_2$ ($PLA_2$) superfamily of enzymes consists of a broad range of enzymes defined by their ability to catalyze the hydrolysis of the ester bond at the sn-2 position of phospholipids, yielding free fatty acids, including arachidonic acid, and lysophospholipids. The characterization and classification of $PLA_2$ enzymes as well as their role in pathophysiological conditions are known. $PLA_2$ enzymes have been systematically classified into 15 groups and subgroups on the basis of their nucleotide and amino acid sequence. According to a broader classification the $PLA_2$ classes have been historically classified into three types: secretory ($sPLA_2$), cytosolic $Ca^{2+}$-dependent ($cPLA_2$) and cytosolic $Ca^{2+}$-independent ($iPLA_2$).

The Group IVA $cPLA_2$ (GIVA $cPLA_2$) is a particularly attractive target for drug development, since it is the rate-limiting provider of arachidonic acid and lysophospholipids that can be converted into prostaglandins, leukotrienes and PAF, respectively. Various studies on gene-targeted mice that lack GIVA $cPLA_2$ showed that prostaglandins and leukotriene production was reduced by approximately 90%, confirming the primacy of GIVA $cPLA_2$ in lipid mediator production. Recently, it was demonstrated that GIVA $cPLA_2$ plays an important role in the pathogenesis of autoimmune encephalomyelitis (which models multiple sclerosis), and that cytosolic phospholipase $A_2$-deficient mice are resistant to experimental autoimmune encephalomyelitis.

The role of the other intracellular $PLA_2$, calcium-independent $PLA_2$ (GVIA $iPLA_2$), in the inflammatory process is still unclear, and it has not been a target for the development of novel medicines. This enzyme appears to be the primary $PLA_2$ for basal metabolic functions within the cell.

It has been shown that in macrophages and other cells, GIVA $cPLA_2$ and secretory phospholipase $A_2$ work together to release arachidonic acid. Several experiments suggest that GV $sPLA_2$ has a role in amplifying the action of GIVA $cPLA_2$ in supplying arachidonic acid for eicosanoid production. In addition, GV $sPLA_2$ has functions independent of its ability to provide arachidonic acid that include regulation of phagocytosis and foam cell formation, suggesting a potential role in inflammatory processes such as atherosclerosis.

Amide phospholipids analogues of substrates can inhibit the activity of secreted $PLA_2$ (e.g., compound 1 shown in FIG. 1). Compound 2 (also shown in FIG. 1) is also as a potent inhibitor of $sPLA_2$. Non-phospholipid amide compounds based on non-natural amino acids, such as compounds 3 and 4 (FIG. 1) can inhibit the activity of pancreatic and non-pancreatic GI and GII $sPLA_2$, and compound 4 has been reported to protect rat small intestine from I/R injury and TNBS-induced colitis.

The selective inhibition of the various $PLA_2$ classes is very important to understand their specific roles in cells and in vivo and develop therapeutic strategies accordingly. Accordingly, a variety of amides based on non-natural amino acids have been synthesized and their specific inhibitory activity on three human $PLA_2$ classes: GIVA $cPLA_2$, GVIA $iPLA_2$, and GV $sPLA_2$ demonstrated as described below in the present application.

SUMMARY OF THE DISCLOSURE

The selective inhibition of the various $PLA_2$ classes is very important to understand their specific roles According to embodiments of the present disclosure, there are provided compounds having the general structure A or pharmaceutically acceptable salts thereof are provided:

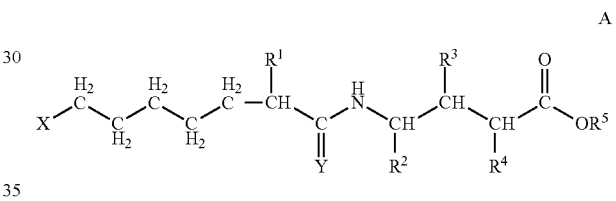

wherein $R^1$ is H, F, $NH_2$, or COOH; $R^2$ is, H, linear saturated or unsaturated alkyl, alkenyl, or alkynyl; each of $R^3$ and $R^4$ is independently H, linear saturated or unsaturated alkyl, alkenyl, alkynyl, phenyl, or substituted phenyl; $R^5$ is H, or ($C_1$-$C_6$)alkyl, such as methyl or ethyl, X is aryl or substituted aryl, such as phenyl or substituted phenyl; and Y is O or S.

Pharmaceutical compositions of inhibitory compounds of the disclosure for use in treating inflammatory conditions for which inhibition of cPLA2, iPLA2 and/or sPLA2 is beneficial are also provided.

DETAILED DESCRIPTION OF THE DISCLOSURE

Figure 1:
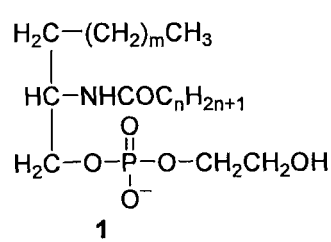
FIG. 1 illustrates several known inhibitors of phospholipases $A_2$.
Figure 1:
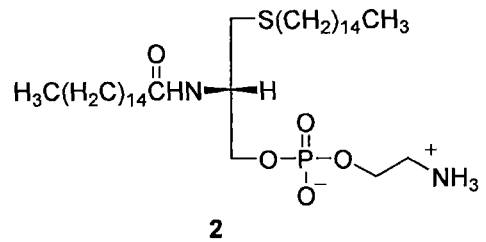
Figure 1:
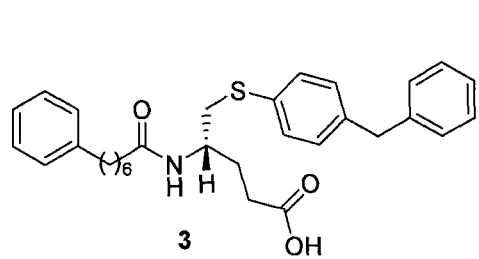
Figure 1:
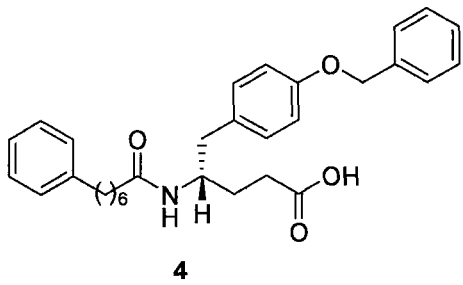

The following non-limiting definitions are provided for ease of reference, and are intended to illustrate, rather than limit, the scope of this disclosure.

The term "alkyl" refers to either substituted or unsubstituted $C_1$-$C_{10}$ straight chain saturated aliphatic hydrocarbon groups, substituted and unsubstituted $C_2$-$C_{10}$ straight chain unsaturated aliphatic hydrocarbon groups, substituted and unsubstituted $C_4$-$C_{10}$ branched saturated aliphatic hydrocarbon groups, substituted and unsubstituted $C_4$-$C_{10}$ branched unsaturated aliphatic hydrocarbon groups, substituted and unsubstituted $C_3$-$C_8$ cyclic saturated aliphatic hydrocarbon groups, substituted and unsubstituted $C_5$-$C_8$ cyclic unsaturated aliphatic hydrocarbon groups having the specified number of carbon atoms. For example, the definition of "alkyl" shall include but is not limited to: methyl, ethyl, propyl, butyl, pentyl, hexyl, heptyl, octyl, nonyl, decyl, undecyl, ethenyl, propenyl, butenyl, penentyl, hexenyl, heptenyl, octenyl, nonenyl, decenyl, undecenyl, isopropyl, isobutyl, tert-butyl, sec-butyl, isopentyl, neopentyl, cyclopropyl, cyclobutyl, cyclopentyl, cyclohexyl, cycloheptyl, cyclooctyl, cyclopentenyl, cyclohexenyl, cycloheptenyl, cyclooctenyl, methylcyclopropyl, ethylcyclohexenyl, butenylcyclopentyl, adamantyl, norbornyl and the like.

Alkyl substituents are independently selected from halogen, —OH, —SH, —$NH_2$, —CN, —$NO_2$, =O, =$CH_2$, trihalomethyl, carbamoyl, aryl$C_{0-10}$alkyl, heteroaryl$C_{0-10}$alkyl, $C_{1-10}$alkyl-oxy, aryl$C_{0-10}$alkyloxy, $C_{1-10}$alkylthio, aryl$C_{1-10}$alkylthio, $C_{1-10}$alkylamino, aryl$C_{0-10}$alkyl-amino, N-aryl-N—$C_{0-10}$alkylamino, $C_{1-10}$alkylcarbonyl, aryl$C_{0-10}$alkylcarbonyl, $C_{1-10}$alkyl-carboxy, aryl$C_{0-10}$alkylcarboxy, $C_{1-10}$alkylcarbonylamino, aryl$C_{0-10}$alkyl-carbonylamino, tetrahydrofuryl, morpholinyl, piperazinyl, hydroxypyronyl, $C_{0-10}$alkylCOO$R_a$ and $C_{0-10}$alkyl-CON$R_bR_c$, wherein $R_a$, $R_b$ and $R_c$ are each independently selected from hydrogen, alkyl, and aryl, or $R_a$ is as describe above, and $R_b$ and $R_c$ are taken together with the nitrogen to which they are attached to form a saturated cyclic or unsaturated cyclic system containing 3 to 8 carbon atoms, optionally with at least one substituent.

The term "aryl" refers to an unsubstituted, mono-, di- or trisubstituted monocyclic, polycyclic, biaryl aromatic groups covalently attached at any ring position capable of forming a stable covalent bond, certain preferred points of attachment being apparent to those skilled in the art (e.g., 3-phenyl, 4-naphtyl and the like). The aryl substituents are each independently selected from halogen, —OH, —SH, —CN, —$NO_2$, trihalomethyl, hydroxypyronyl, $C_{1-10}$alkyl, aryl$C_{0-10}$alkyl, $C_{0-10}$alkyloxy$C_{0-10}$alkyl, aryl$C_{0-10}$alkyloxy-$C_{0-10}$alkyl, $C_{0-10}$alkylthio$C_{0-10}$alkyl, aryl$C_{0-10}$alkylthio$C_{0-10}$alkyl, $C_{0-10}$alkylamino$C_{0-10}$alkyl, aryl$C_{0-10}$alkylamino$C_{0-10}$alkyl, N-aryl-N—$C_{0-10}$alkylamino$C_{0-10}$alkyl, $C_{1-10}$alkylcarbonyl-$C_{0-10}$alkyl, aryl$C_{0-10}$alkylcarbonyl$C_{0-10}$alkyl, $C_{1-10}$alkylcarboxy$C_{0-10}$alkyl, aryl$C_{0-10}$alkyl-carboxy$C_{0-10}$alkyl, $C_{1-10}$alkylcarbonylamino$C_{0-10}$alkyl, aryl$C_{0-10}$alkylcarbonylamino$C_{0-10}$alkyl, alkylCOO$R_a$, and —$C_{0-10}$alkylCON$R_bR_c$, wherein $R_a$, $R_b$ and $R_c$ are each independently selected from hydrogen, alkyl, and aryl; or $R_a$ is as described above, and $R_b$ and $R_c$ are taken together with the nitrogen to which they are attached to form a saturated cyclic or unsaturated cyclic system containing 3 to 8 carbon atoms, optionally with at least one substituent.

The definition of "aryl" includes, but is not limited to, such specific groups as phenyl, biphenyl, naphthyl, dihydronaphthyl, tetrahydronaphthyl, indenyl, indanyl, azulenyl, anthryl, phenanthryl, fluorenyl, pyrenyl and the like.

The terms "halogen", "halide" or "halo" refer to fluorine, chlorine, bromine, and iodine.

The abbreviation "BOC" refers to tert-butoxycarbonyl moiety having the structure —C(O)—O—C(CH$_3$)$_3$.

The abbreviation "TEMPO" refers to teramethylpiperidin-1-oxyl moiety having the structure:

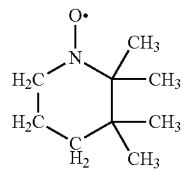

The term "effective amount" of a compound refers a non-toxic but sufficient amount of the compound that provides a desired effect. This amount may vary from subject to subject, depending on the species, age, and physical condition of the subject, the severity of the disease that is being treated, the particular compound used, its mode of administration, and the like. Therefore, it is difficult to generalize an exact "effective amount," yet, a suitable effective amount may be determined by one of ordinary skill in the art.

The term "pharmaceutically acceptable" refers to a compound, additive or composition that is not biologically or otherwise undesirable. For example, the additive or composition may be administered to a subject along with a compound of the disclosure without causing any undesirable biological effects or interacting in an undesirable manner with any of the other components of the pharmaceutical composition in which it is contained.

The term "pharmaceutically acceptable salts" includes hydrochloric salt, hydrobromic salt, hydroiodic salt, hydrofluoric salt, sulfuric salt, citric salt, maleic salt, acetic salt, lactic salt, nicotinic salt, succinic salt, oxalic salt, phosphoric salt, malonic salt, salicylic salt, phenylacetic salt, stearic salt, pyridine salt, ammonium salt, piperazine salt, diethylamine salt, nicotinamide salt, formic salt, urea salt, sodium salt, potassium salt, calcium salt, magnesium salt, zinc salt, lithium salt, cinnamic salt, methylamino salt, methanesulfonic salt, picric salt, tartaric salt, triethylamino salt, dimethylamino salt, tris(hydroxymethyl)aminomethane salt and the like. Additional pharmaceutically acceptable salts are known to those of skill in the art.

As used herein, the term "patient" refers to organisms to be treated by the methods of the present disclosure. Such organisms include, but are not limited to, humans. In the context of the disclosure, the term "subject" generally refers to an individual who will receive or who has received treatment for the treatment of a disease, disorder or pathology.

According to embodiments of the present disclosure, there are provided compounds having the general structure A or pharmaceutically acceptable salts thereof:

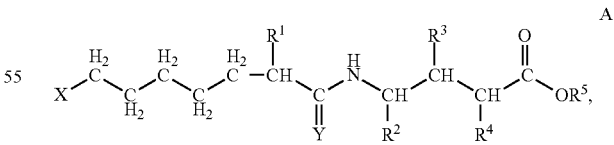

wherein $R^1$ is H, F, $NH_2$, or COOH; $R^2$ is, H, or a linear saturated or unsaturated alkyl, alkenyl, or alkynyl; each of $R^3$ and $R^4$ is H, a linear saturated or unsaturated alkyl, alkenyl, or alkynyl, phenyl, or a substituted phenyl; $R^5$ is H, methyl, or ethyl, X is an aryl or a substituted aryl, such as phenyl or a substituted phenyl; and Y is O or S.

One specific example of a useful compound encompassed by the genius of the general structure A is a compound where each of $R^1$, $R^3$, $R^4$, and $R^5$ is H, $R^2$ is n-butyl, X is phenyl, and Y is O (i.e. (R)-4-(7-phenylheptanamido)octanoic acid, or compound 9 shown below):

Compound 9

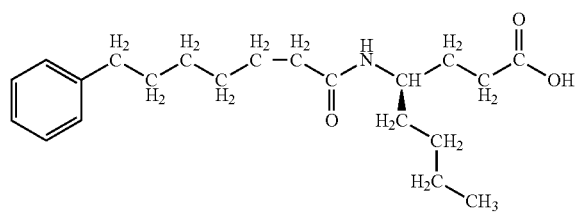

Various synthetic schemes can be designed for manufacturing the products having the structure A, including the specific compound 9. To exemplify, but not limit, the present disclosure, in one embodiment, the reaction scheme I shown below can be employed for making such compounds. If desired, other synthetic processes can be designed by those having ordinary skill in the art.

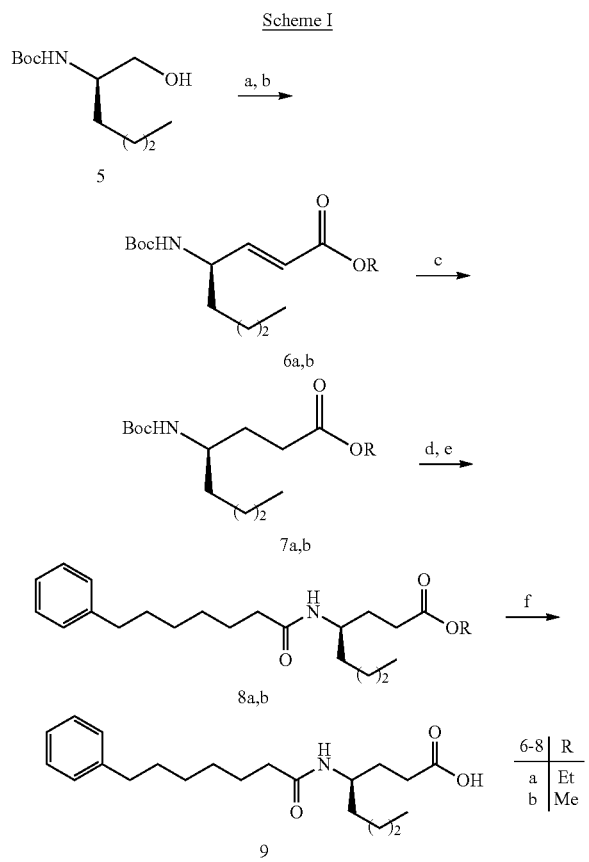

More detailed discussion of the conditions and the results of the synthesis shown by the reaction scheme I is provided below, in the "Examples" portion of the present application.

The following examples are intended to further illustrate but not limit the scope of the disclosure. Standard abbreviations (e.g., "ml" for milliliters, and "min." for minutes) are used.

EXAMPLES

Example 1

Synthesis of (R)-4-(7-phenylheptanamido)octanoic acid

The synthesis of a γ-norleucine-based amide containing the 7-phenylheptanoyl chain was conducted as shown by the reaction scheme I shown above. Starting compound 5 (i.e., Boc-D-norleucinol) prepared according to the previously known techniques, was oxidized to aldehyde (step (a) on the reaction scheme I) using NaOCl, TEMPO, NaBr, and $NaHCO_3$. A 3:3:0.5 mixture of athyl acetate, toluene and water was used as a solvent system. The reaction of oxidation was carried out at a temperature of about −5° C. As a step (b) shown by the reaction scheme I, methyl(phosphoranylidene)acetate $Ph_3P$=CHCOOMe or, alternatively, ethyl(phosphoranylidene)acetate $Ph_3P$=CHCOOEt in tetrahydrofuran was added and the system was brought to produce either compounds 6b or compound 6a, respectively, as shown on the reaction scheme I.

After hydrogenation and removal of Boc group, using $H_2$, 10% Pd/C, and methanol (step (c) shown by the reaction scheme I), coupling with 7-phenylheptanoic acid gave amides 8a,b. The process of coupling was conducted using 4N hydrochloric acid in ethyl ether (step (d) shown by the reaction scheme I), and $Ph(CH_2)_6COOH$ (i.e., 7-phenylheptanoic acid), 1-ethyl-3-(3-dimethylaminopropyl)carbodiimide (i.e., WSCI), butyl alcohol, triethylamine, and dichloromethane (step (e) shown by the reaction scheme I).

The title compound 9 was then obtained after saponification of either 8a or 8b the final step (f) shown by the reaction scheme I). 1N NaOH in dioxane was used for saponification. The of the enantiomer of the title compound 9 was synthesized following similar reactions.

Example 2

In Vitro Inhibition of GIVA $cPLA_2$, GVIA $iPLA_2$ and GV sPLA2

Figure 2:
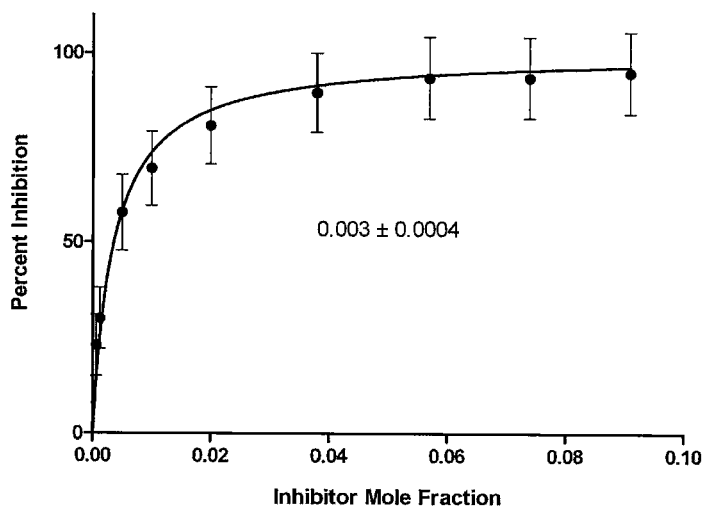
FIG. 2 illustrates inhibition curve for an amide of the present disclosure in a mixed-micelle assay with human GV $sPLA_2$.

Compound 9 based on (R)-γ-norleucine is a potent and selective GV $sPLA_2$ inhibitor, not affecting at all the activities of GIVA $cPLA_2$ and GVIA $iPLA_2$. The dose-response curve for the inhibition of GV $sPLA_2$ by compound 9 is shown in FIG. 2, and a non-linear regression (hyperbolic) led to the calculation of $X_I(50)$ value of 0.003±0.0004. The configuration of the amino acid is important, since its enantiomer based on (S)-γ-norleucine was inactive for all the three $PLA_2$ enzymes.

The amides were tested for inhibition of human GIVA $cPLA_2$, GVIA $iPLA_2$ and GV $sPLA_2$ using previously described mixed micelle-based assays. The resulting degrees of inhibition are presented as either percent inhibition or $X_I(50)$ values. Initially, the percent of inhibition for each $PLA_2$ enzyme at 0.091 mole fraction of each inhibitor was determined, and, $X_I(50)$ values were estimated for compounds that displayed greater than 90% inhibition. The $X_I(50)$ is the mole fraction of the inhibitor in the total substrate interface required to inhibit the enzyme by 50%. Compound 9 did not inhibit GIVA $cPLA_2$ and GVIA $iPLA_2$ at 0.091 mole fraction.

Example 3

Effects of Compound 9 in Spinal Cord Injury (SCI)

Figure 3:
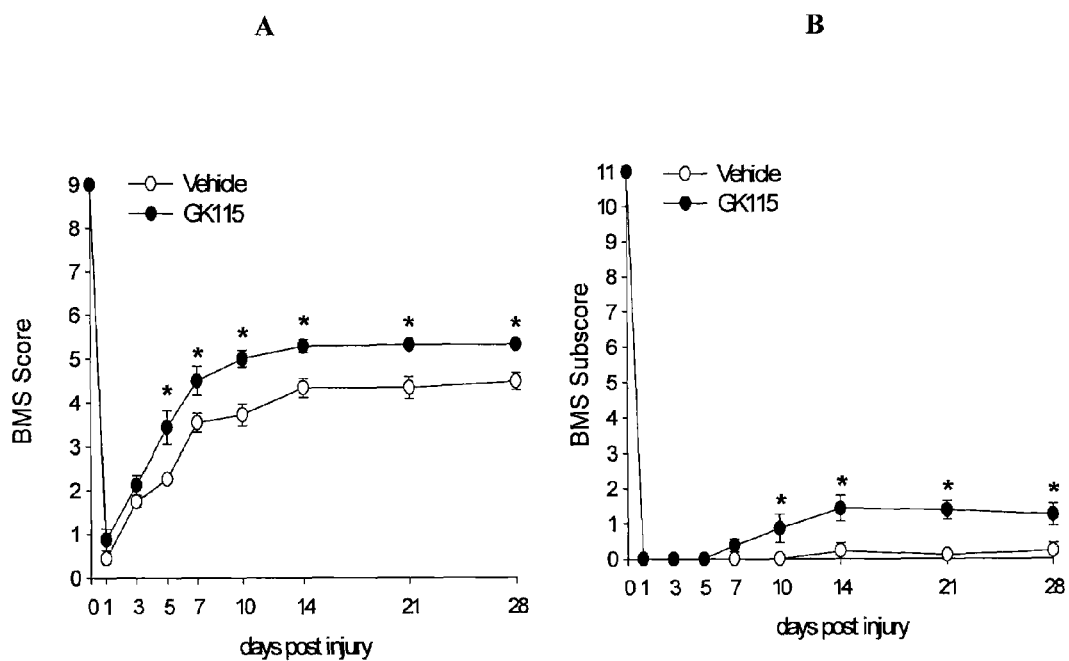
FIG. 3 illustrates the assessment of locomotor recovery after spinal cord injury (SCI) and administration of compound 9.

FIG. 3 illustrates the assessment of locomotor recovery after SCI. (A) Administration of compound 9 started 1 hour after SCI improved locomotor function assessed using the 9-point Basso Mouse Scale (BMS) as compared with the vehicle treated mice. Post-hoc analysis revealed significant differences in BMS score starting at day 5 dpi and remaining significantly enhanced during the duration of the follow up. (B) Fine locomotor skills assessed by the BMS subscores also showed a significant improvement in mice treated with compound 9 from day 10 to 28 after SCI. *p<0.05.

Figure 4:
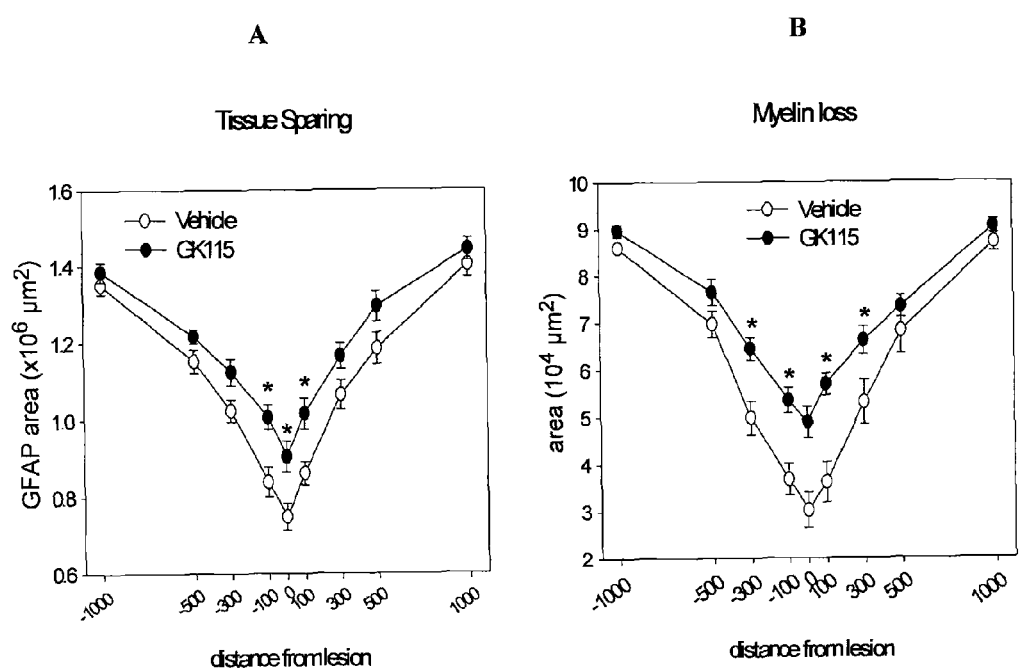
FIG. 4 illustrates the quantification of tissue and myelin sparing in mice treated with compound 9.

FIG. 4 illustrates the quantification of tissue and myelin sparing assessed by staining for GFAP and luxol fast blue, respectively, at 28 days after SCI. (A) Mice treated with compound 9 displayed a significant reduction tissue loss in tissue sections at 100 µm rostral and caudal to the lesion epicenter. (B) Compound 9 treatment also led to significant myelin sparing at the epicenter and areas rostral and caudal to it.

Figure 5:
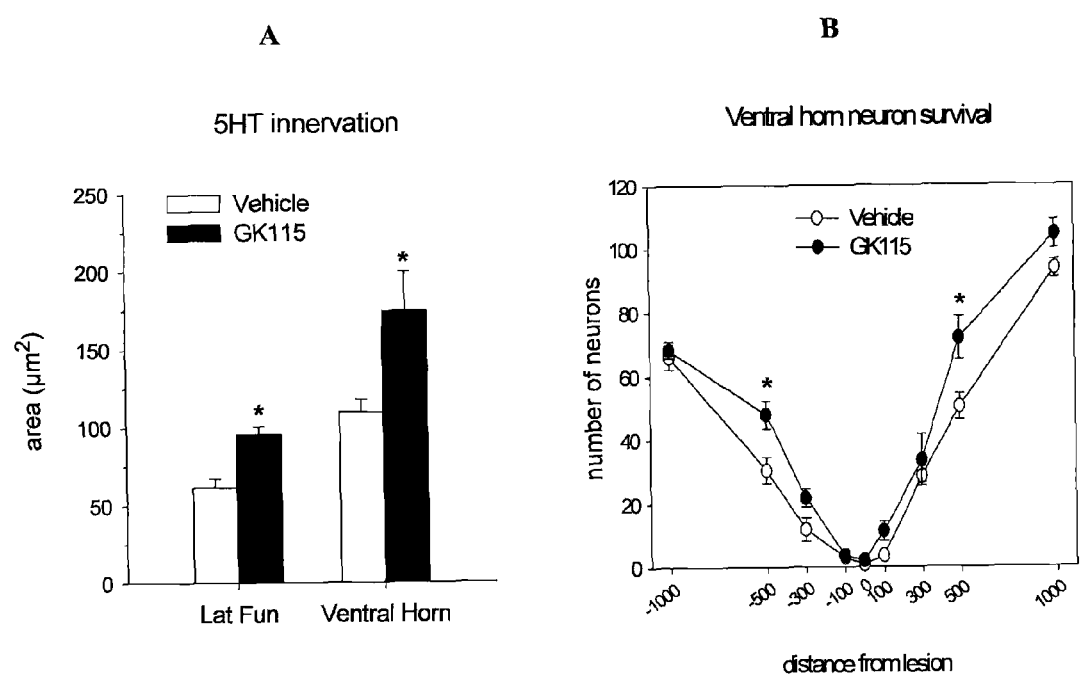
FIG. 5 illustrates the quantification of serotonergic fiber sparing and neuronal survival at 28 after SCI in mice treated with compound 9.

FIG. 5 illustrates the quantification of serotonergic fiber sparing and neuronal survival at 28 after SCI. (A) Mice treated with compound 9 displayed significantly greater serotonergic sparing in the ventral horns 1 mm caudal to the lesion epicenter. (B) Compound 9 also promoted greater neuron survival in tissue section at 500 µm rostral and caudal to the lesion epicenter.

described in terms of Markush groups, those skilled in the art will recognize that the disclosure is also thereby described in terms of any individual member or subgroup of members of the Markush group. Further, the references appended hereto are all incorporated herein by this reference.

What is claimed is:

1. A compound having the structure A, or pharmaceutically acceptable salts thereof:

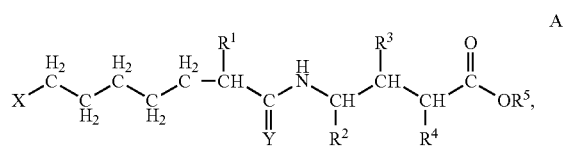

wherein:

$R^1$ is H, F, $NH_2$, or COOH;

$R^2$ is H, linear saturated or unsaturated unsubstituted ($C_2$-$C_{10}$)alkyl, alkenyl, or alkynyl;

each of $R^3$ and $R^4$ is independently H, linear saturated or unsaturated alkyl, alkenyl, alkynyl, phenyl, or substituted phenyl;

| | | Inhibition (% at 0.091 mol fraction) | | |
|---|---|---|---|---|
| Inhibitor | Structure | cPLA$_2$ GIVA | iPLA$_2$ GVIA | sPLA$_2$ GIIA/GV* |
| AX115[1] | ![structure] | 62 ± 1 | 45 ± 13 | 52 ± 4 |
| FKGK11[2] | ![structure] | N.D. | >95 $X_I(50) =$ 0.0096 ± 0.0008 | 28 ± 1 |
| Compound 9[1] | ![structure] | N.D. | N.D. | >95 $X_I(50) =$ 0.003 ± 0.0004 |

EXAMPLE 4. Inhibition of PLA$_2$ by Synthetic Inhibitors[a]

[a]Average percent inhibition and standard error (n = 3) reported for each compound at 0.091 mole fraction. $X_I(50)$ values determined for inhibitors with greater than 95% inhibition. N.D. signifies compounds with less than 25% inhibition (or no detectable inhibition).

References:

[1] "STRUCTURE-ACTIVITY RELATIONSHIPS OF NATURAL AND NON-NATURAL AMINO ACID-BASED AMIDE AND 2-OXOAMIDE INHIBITORS OF HUMAN PHOSPHOLIPASE A$_2$ ENZYMES" G. Antonopoulou, E. Barbayianni, V. Magrioti, N. Cotton, D. Stephens, V. Constantinou-Kokotou, E. A. Dennis, and G. Kokotos Bioorg. Med. Chem. 2008, 16, 10257-10269.

[2] "SYNTHESIS OF POLYFLUORO KETONES FOR SELECTIVE INHIBITION OF HUMAN PHOSPHOLIPASE A$_2$ ENZYMES" C. Baskakis, V. Magrioti, N. Cotton, D. Stephens, V. Constantinou-Kokotou, E. A. Dennis and G. Kokotos J. Med. Chem. 2008, 51, 8027-8037.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

Other embodiments are within the following claims. In addition, where features or aspects of the disclosure are $R^5$ is H or ($C_1$-$C_6$)alkyl;

X is aryl or substituted aryl; and

Y is O or S.

2. The compound of claim 1, wherein $R^5$ is H, methyl, or ethyl; and X is phenyl or substituted phenyl.

3. The compound of claim 1, wherein the compound has the formula 9:

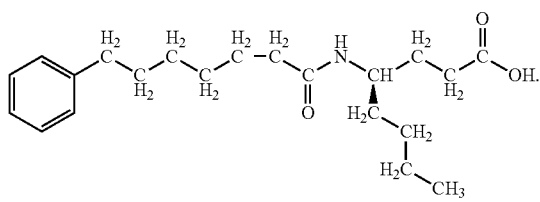 [SMILES: CCCC[C@H](CCC(=O)O)NC(=O)CCCCCCc1ccccc1]

4. A method of inhibiting a phoshpolipase $A_2$, comprising contacting the phoshpolipase $A_2$ with a compound having the structure A, or pharmaceutically acceptable salts thereof:

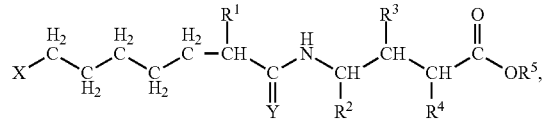

wherein:
$R^1$ is H, F, $NH_2$, or COOH;
$R^2$ is H, linear saturated or unsaturated unsubstituted ($C_2$-$C_{10}$)alkyl, alkenyl, or alkynyl;
each of $R^3$ and $R^4$ is independently H, linear saturated or unsaturated alkyl, alkenyl, alkynyl, phenyl, or substituted phenyl;
$R^5$ is H or ($C_1$-$C_6$)alkyl;
X is aryl or substituted aryl; and
Y is O or S.

5. The method of claim 4, wherein $R^5$ is H, methyl, or ethyl; and X is phenyl or substituted phenyl.

6. The method of claim 4, wherein the compound has the formula 9:

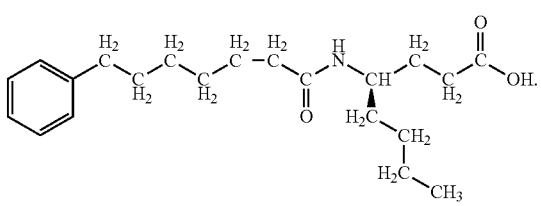

* * * * *